United States Patent
Amanatullah

(10) Patent No.: US 11,478,302 B2
(45) Date of Patent: Oct. 25, 2022

(54) METHODS FOR GENERATING INTRAOPERATIVE SURGICAL GUIDANCE DURING JOINT ARTHROPLASTY BASED ON DYNAMIC LIGAMENT TENSION

(71) Applicant: Arthrology Consulting, LLC, Palo Alto, CA (US)

(72) Inventor: Derek Amanatullah, Palo Alto, CA (US)

(73) Assignee: Arthrology Consulting, LLC, Palo Alto, CA (US)

( * ) Notice: Subject to any disclaimer, the term of this patent is extended or adjusted under 35 U.S.C. 154(b) by 239 days.

(21) Appl. No.: 16/886,413

(22) Filed: May 28, 2020

(65) Prior Publication Data
US 2020/0383729 A1 Dec. 10, 2020

Related U.S. Application Data

(60) Provisional application No. 62/853,600, filed on May 28, 2019.

(51) Int. Cl.
*A61B 34/10* (2016.01)
*A61B 17/15* (2006.01)
*A61B 90/00* (2016.01)

(52) U.S. Cl.
CPC ............ *A61B 34/10* (2016.02); *A61B 17/154* (2013.01); *A61B 90/06* (2016.02); *A61B 2034/105* (2016.02); *A61B 2090/064* (2016.02)

(58) Field of Classification Search
CPC ............ A61B 17/154; A61B 2034/105; A61B 2090/064; A61B 2090/065; A61B 34/10; A61B 90/06
See application file for complete search history.

(56) References Cited

U.S. PATENT DOCUMENTS

2016/0278754 A1* 9/2016 Todorov ................ A61F 2/3859

\* cited by examiner

*Primary Examiner* — Samuel S Hanna
(74) *Attorney, Agent, or Firm* — Run8 Patent Group, LLC; Peter Miller

(57) ABSTRACT

A method for generating intraoperative surgical guidance during a knee arthroplasty includes: preceding resection of a first bone and a second bone in a knee of a patient, generating a first ligament tension curve for a first ligament in the knee; generating a second ligament tension curve for a second ligament in the knee; storing a first target tension curve for the first ligament based on the first ligament tension curve; and, succeeding resection of the first bone and succeeding placement of a first test implant on the first bone, generating a third ligament tension curve for the first ligament; characterizing a first phase difference between the third ligament tension curve and the first target tension curve; and in response to the first phase difference exceeding a threshold negative phase difference, outputting a first prompt to a surgeon to further resect the first bone proportional to the first phase difference.

18 Claims, 5 Drawing Sheets

METHODS FOR GENERATING INTRAOPERATIVE SURGICAL GUIDANCE DURING JOINT ARTHROPLASTY BASED ON DYNAMIC LIGAMENT TENSION

CROSS-REFERENCE TO RELATED APPLICATIONS

This Application claims the benefit of U.S. Provisional Patent Application No. 62/853,600, filed on 28 May 2019, which is incorporated in its entirety by this reference.

This Application is related to U.S. patent application Ser. No. 15/499,046, filed on 27 Apr. 2017, which is incorporated in its entirety by this reference.

TECHNICAL FIELD

This invention relates generally to the field of arthroplasty and more specifically to a new and useful method for generating intraoperative guidance during joint arthroplasty based on dynamic ligament tension in the field of arthroplasty.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. First Method

Figure 1:
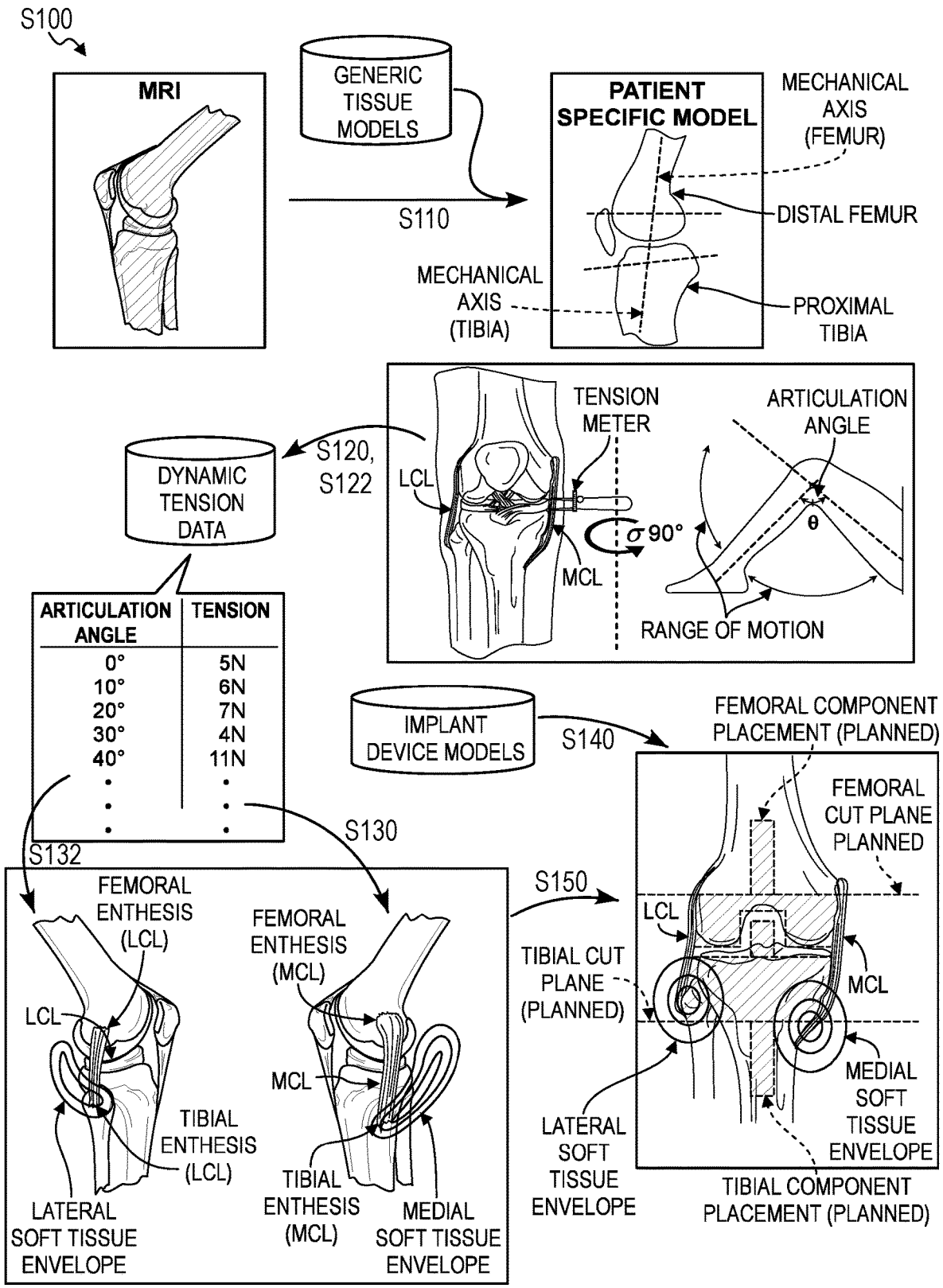
FIG. 1 is a flowchart representation of a first method.

As shown in FIG. 1, a first method S100 method for generating intraoperative guidance during joint arthroplasty based on dynamic ligament tension includes: detecting bony anatomy of a patient, the bony anatomy of the patient comprising an axis of a femur of the patient, an axis of a tibia of the patient, geometry of a distal femur of the patient, and geometry of a proximal tibia of the patient in Block S110; accessing medial dynamic tension data for a medial collateral ligament of the patient comprising a measurement of tension in the medial collateral ligament corresponding to each of a set of angles of articulation of a knee of the patient in Block S120; accessing lateral dynamic tension data for a lateral collateral ligament of the patient comprising a measurement of tension in the lateral collateral ligament corresponding to each of a set of angles of articulation of the knee of the patient in Block S122; calculating a medial soft tissue envelope of the medial collateral ligament relative to the axis of the femur based on the medial dynamic tension data in Block S130; calculating a lateral soft tissue envelope of the lateral collateral ligament relative to the axis of the femur based on the lateral dynamic tension data in Block S132; accessing a model of an implant comprising a femoral component and a tibial component in Block S140; and calculating a trajectory of a femoral cut relative to the axis of the femur, a placement of the femoral component, a trajectory of a tibial cut relative to the axis of the tibia, and the placement of a tibial component, based on the geometry of the distal femur, the geometry of the proximal tibia, the model of the implant, the medial soft tissue envelope, and the lateral soft tissue envelope in Block S150.

1.1 Applications

Figure 2:
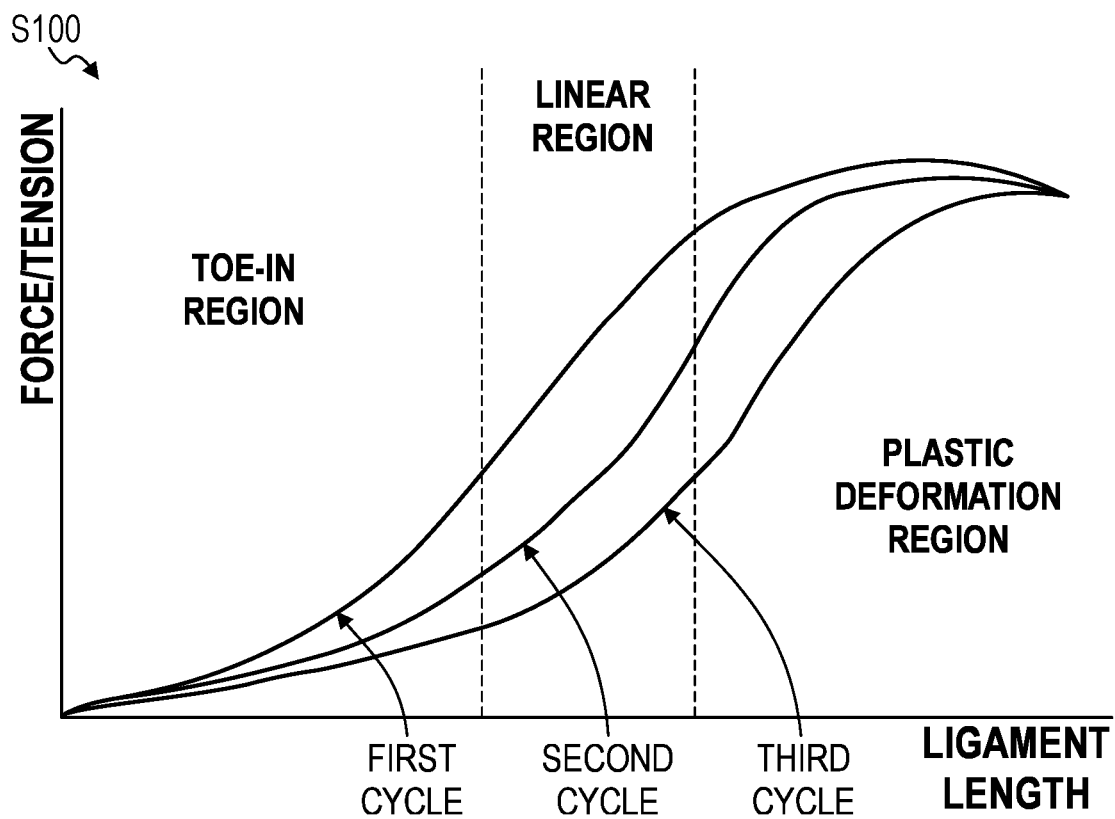
FIG. 2 is a graphical representation one variation of the first method.

Generally, the first method S100 can be executed by a computer system (hereinafter "the system") during a knee arthroplasty procedure in order to: detect the bony anatomy of a patient; access dynamic tension data from the ligaments of the patient prior to resection of bony tissue; and designate an implant (including a femoral component and a tibial component) for the patient before calculating a trajectory of a femoral cut, a placement of a femoral component, a trajectory of a tibial cut, and a placement of a tibial component, such that the placement of the designated implant conforms with the bony anatomy of the patient and the ligaments of the patient track within acceptable "soft tissue envelopes" defined by the dynamic tension data. More specifically, the system can calculate a preoperative plan, including initial cut trajectories and implant placements, that satisfies target postoperative ligament tensions and/or ligament lengths in the patient based on dynamic tension data obtained from the patient and patient-specific anatomy. Furthermore, the system can update the preoperative plan in real-time as the surgery progresses (e.g., as the surgeon resects the femoral head) in order to mitigate compounding positional errors as they affect target postoperative ligament tension and/or target postoperative ligament length, as shown in FIG. 2.

Thus, the first method S100 improves total knee arthroplasty procedures by accurately predicting postoperative tension via definition of a "soft-tissue envelope" for each relevant ligament and by recommending cuts and implant placements concordant with the soft-tissue envelope. For a total knee arthroplasty, the system can define a lateral soft tissue envelope for a patient's lateral collateral ligament (hereinafter "LCL") and a medial soft tissue envelope for the patient's medial collateral ligament (hereinafter "MCL"), wherein the soft tissue envelope defines a volume in three-dimensional space (e.g., relative a constrained feature of a patient's anatomy) where the system predicts that the ligament will exhibit an acceptable tension when one enthesis of the ligament is located within the soft tissue envelope. For example, the system can define a soft tissue envelope for the tibial attachment of a patient's MCL relative to the femoral attachment of the patient's MCL that approximates a satisfactory tension of the MCL throughout the range of motion of the MCL and throughout multiple dynamic cycles of elongation of the MCL of the patient.

Prior to a total knee arthroplasty for a patient, the system can detect the anatomy, such as the bony and/or soft tissue anatomy of the patient by accessing two-dimensional (hereinafter "2D") or three-dimensional (hereinafter "3D") diagnostic scans of a patient's knee in order to construct a patient-specific model of the anatomy of the patient. Additionally, the system can access images from the operating room (e.g., via an overhead camera or LIDAR) and update the patient-specific model in real-time based on observed anatomical deviations from the original patient-specific model generated according to preoperative scans of the patient. The patient-specific model can approximate regions of the patient's bony anatomy, such as the patient's distal femur, proximal tibia, and patella. Additionally, the system can also locate attachment sites for ligaments of the patient, such as the femoral and tibial entheses of the MCL of the patient and the femoral and tibial entheses of the LCL of the patient.

Upon initiating a total knee arthroplasty, the surgeon may obtain dynamic tension data from the patient prior to performing femoral or tibial cuts, such as by dynamically measuring the tension of the patients MCL and LCL throughout the range of motion of the patient's knee. In one implementation, the surgeon may record the tension in the patient's MCL and LCL over a set of discrete articulation angles. Additionally or alternatively, the surgeon may place an inertial measurement unit (hereinafter "IMU") on an anatomical reference position on the patient's tibia while recording synchronized measurements of tension in the patient's MCL and LCL in order to correlate each tension measurement with a particular articulation angle of the knee. The system can then access the dynamic tension data for each ligament in order to identify a soft tissue envelope for each ligament. In one implementation, the system can aid the surgeon in obtaining the dynamic tension data by optically tracking (e.g., via one or more cameras positioned throughout the operating room and computer vision techniques) the articulation angle of the patient's knee as the surgeon measures the tension on the patient's ligaments throughout the patient's range of motion. The system can then access the tension measurements in real-time to synchronize each tension measurement on each tendon with the articulation angle of the patient's knee when the tension measurement was recorded.

Once the system accesses the dynamic tension data for the MCL and/or LCL of the patient, the system can define a medial soft tissue envelope and a lateral soft tissue envelope that define an acceptable range of motion for the MCL and LCL respectively. The system can then select an implant that, given a specific placement, can maintain the MCL and LCL of the patient within the medial soft tissue envelope and the lateral soft tissue envelope respectively. Alternatively, the system can receive an implant selection from a surgeon via a surgeon portal (e.g., a graphical user interface). After the implant has been designated, the system can access a 3D model of the femoral, tibial, and/or patellar components of the implant. Furthermore, the system can calculate a placement of the femoral, tibial, and/or patellar component of the implant relative to the patient-specific model according to mechanical and/or kinematic constraints of the knee and while maintaining ligament tension by matching the range of motion of the MCL and LCL as closely as possible to the medial soft tissue envelope and lateral soft tissue envelope respectively.

Subsequently, and based on the calculated placement of the implant, the system can generate a surgical plan comprising femoral cut trajectories, tibial cut trajectories, and/or one or more patellar cut trajectories according to a specified installation procedure for the implant. Additionally, as the surgeon operates according to the surgical plan, the system can monitor the surgeon's progress in the surgical plan and adjust subsequent steps in the surgical plan based on prior deviations from the surgical plan in order to maintain the target tension in the patient's MCL and LCL and to accurately mechanically and/or kinematically align. Furthermore, the system can prompt the surgeon to revise an already completed surgical step. For example, after the surgeon resects a patient's femur, the system can prompt the surgeon to resect the patient's femur by an additional 3 mm in order to comply with the surgical plan.

Thus, according to the above described steps, the system can plan and/or guide a surgeon through a total knee arthroplasty procedure by calculating and updating a surgical plan designed to affect a target postoperative tension in the patient's MCL and LCL while also obtaining proper postoperative mechanical and/or kinematic alignment of the patient's knee.

For ease of explanation, Blocks of the first method S100 are described with respect to a total knee arthroplasty. However, the first method S100 can be applied to other surgical procedures involving the replacement of a patient's joint with a prosthesis such as total hip arthroplasty, partial knee arthroplasty, total shoulder arthroplasty, or any other arthroplasty procedure.

Additionally, Blocks of the first method S100 are described herein with respect to a patient's MCL and LCL however, the system can likewise apply blocks of the method S100 to other ligaments and tendons associated with a knee joint or any other joint of the patient (e.g., the patient's ACL and PCL in the case of the a partial knee arthroplasty).

Furthermore, for ease of explanation, the method S100 is described with generic reference to a knee of a patient without specifying a "right knee" or a "left knee" of a patient. However, the system can execute Blocks of the first method S100 with respect to either knee of the patient undergoing a total knee arthroplasty. Therefore, refences to anatomy of the patient generally refers to one side of the patient's body (e.g., the phrase "a patient's MCL and LCL" refers to either the patient's right MCL and the patients right LCL or the patient's left MCL and the patient's left LCL).

Generally, the system can generate various types of "models" (e.g., patient-specific models, generic tissue models, femur models, tibia models, implant models) in a virtual 3D space. Therefore, the system can orient, position, or otherwise transform these models relative to each other in the virtual 3D space. Additionally, the system can rotationally and/or laterally constrain the models relative to each other for the purpose of simulating movement of a patient's joint. Furthermore, the system can estimate the physical characteristics (e.g., elasticity, density, kinetic and static friction) of each tissue type simulated in a model.

1.2 Examples

The system can execute Blocks of the first method S100 to provide guidance to a surgeon during a surgical procedure in selecting from a number of corrective options available at each step in a surgical arthroplasty procedure including: selecting a new implant, resecting bony tissue, adding spacers between bony tissue and an implant, or resecting ligamentous tissue. Therefore, the system can continuously reevaluate the surgical environment based on prior changes to the bony anatomy, soft tissue anatomy, or placement of implant components. Furthermore, in guiding the surgeon in selecting from amongst the aforementioned decisions, the system can execute Blocks of the method S100 to position an implant or cut in all six degrees of freedom such as proximal/distal, anterior/posterior, medial/lateral, varus/valgus, flexion/extension, internal/external rotation (e.g., relative to the femur in a knee arthroplasty procedure).

Additionally, the processes involved in executing the method S100 can be executed by the system in any order such that the system can predict the potential effects (in terms of ligament balance) of any surgical decision. For example, the system can predict the effects of resecting a tendon, resecting additional bone tissue, changing an implant component at any time during a surgical procedure.

1.3 Patient Anatomy Detection

In Block Silo of the first method S100, the system detects the bony anatomy of a patient, which can include an axis of a femur of the patient, an axis of a tibia of the patient, geometry of a distal femur of the patient, and geometry of a proximal tibia of the patient in Block Silo. More specifically, the system can access 2D or 3D MRI, CAT, X-ray, or other scan data of a region of a patient's body designated for an upcoming surgery; and implement edge detection, pattern matching, object recognition, and/or any other computer vision method or technique to automatically identify discrete tissue masses—such as skin, bone, cartilage, blood vessels, lymph nodes, muscle, and/or nerve tissue—in the scan data. Based on types and relative positions of discrete tissues thus identified in the scan data, the system can identify various aspects of the bony anatomy of the patient including the distal femur of the patient and proximal tibia of the patient and/or the patella of the patient.

In one example, for a surgeon preparing for a total knee replacement in a patient's right knee, the system can: access a 3D MRI scan of the patient's right leg from approximately eight inches below the tibial condyle to approximately eight inches above the femoral condyle; and transform this 3D MRI scan into a 3D point cloud, wherein each point in the 3D point cloud is labeled with a tissue density from a corresponding region of the 3D MRI scan. The system can then identify clusters of points with like tissue density labels in the 3D point cloud, identify boundaries between distinct clusters of points with like tissue density labels, and group contiguous clusters of points with like tissue density labels as discrete tissue masses in the 3D point cloud. The system can also implement known tissue density ranges for various types of tissue—such as a tissue density range for each of skin, bone, cartilage, blood vessels, lymph nodes, muscle, and/or nerve tissue—to label each point of a discrete tissue mass in the 3D point cloud with a particular tissue type. The system can then: retrieve a generic tissue model of a right leg, including anatomical tissue labels; globally and/or locally scale, articulate, rotate, translate, or otherwise manipulate the generic leg model to approximately align discrete tissue models in the generic leg model with discrete tissue masses of similar tissue densities, types, geometries, and/or relative positions (e.g., relative to other tissue types) in the 3D point cloud; and transfer anatomical tissue labels (e.g., MCL, LCL, iliotibial band, hamstring tendon, patellar tendon, lateral patellar retinaculum, patella, quadriceps, tibia, femur, etc.) from the generic leg model to the 3D point cloud.

Alternatively, the system can implement template matching techniques to match template tissue point clouds—labeled with one or more anatomical tissue labels—to tissue masses identified in the 3D point cloud and transfer anatomical tissue labels from matched template tissue point clouds to corresponding tissue masses in the 3D point cloud. Yet alternatively, the system can: implement computer vision techniques, such as edge detection or object recognition, to automatically detect distinct tissue masses in the scan data; and write an anatomical tissue label to each distinct tissue mass in the 3D point cloud based on anatomical tissue labels manually entered or selected by the surgeon through the surgeon portal. However, the system can implement any other method or technique to label tissues within patient scan data automatically or with guidance from a surgeon.

Alternatively, the system can interface with the surgeon through a surgeon portal to: manually identify discrete tissues in patient scan data; to align a generic tissue model to patient scan data; to locate one or more implant models, surgical tools, surgical guides, surgical fasteners, etc. relative to the patient's scan data or relative to an object in a patient-specific tissue model; and/or to define a cut plane or a cutting tool trajectory for an upcoming surgery. The system can thus construct a surgical environment depicting both patient tissue and one or more surgical objects based on data entered by a surgeon, radiologist, etc. However, the system can implement any other method or technique to automatically—or with guidance from one or more surgeons, radiologists, nurses, etc.—to generate a 3D (or 2D, or 4D) model defining a surgical plan for an upcoming surgery.

In one variation, the system can scale, articulate, translate, rotate, or otherwise manipulate tissue objects within a generic tissue model of a similar region of a human body into alignment with corresponding labeled tissue masses in the 3D point cloud. For example, the system can: locally scale and reorient surfaces of a generic tibia model to mimic the geometry of a tibia labeled in the 3D point cloud thereby generating a patient-specific tibia model; locally scale and reorient surfaces of a generic quadriceps muscle model to mimic the geometry of a quadriceps muscle labeled in the 3D point cloud thereby generating a patient-specific quadriceps muscle model; locally scale and reorient surfaces of a generic iliotibial band model to mimic the geometry of a iliotibial band labeled in the 3D point cloud thereby generating a patient-specific iliotibial band model; and locally scale and reorient a generic skin model—around the patient-specific tibia model, the patient-specific quadriceps muscle model, and the patient-specific iliotibial band model—to mimic the geometry of the exterior of the patient's leg shown in the 3D point cloud thereby generating a patient-specific skin model. The system can thus generate a patient-specific tissue model of a region of the patient's body scheduled for surgery by merging real patient scan data with a generic tissue model of a human body or region of a human body In one implementation, the system can generate a patient-specific model of the knee joint region (i.e. a patient-specific knee joint model) according to the variation described above, wherein the patient-specific knee joint model can include a distal femur model and a proximal tibia model each with articular cartilage, a patella model, a medial and lateral meniscus model, an anterior cruciate ligament (hereinafter "ACL") model, a posterior cruciate ligament (hereinafter "PCL") model, and/or an MCL model, and an LCL model (including the MCL entheses and the LCL entheses). Furthermore, the system can generate a postoperative patient-specific model of a patient's knee joint region further including a femoral component model, a tibial component model, and/or a patellar component model. Upon generating a patient-specific knee joint model, the system can simulate articulation of the knee under load (e.g., based on the patient's weight) and model the tension in the ligament models throughout articulation of the knee joint model.

Once the system has detected the bony anatomy of the patient in 3D space, the system can derive the position of mechanical and/or kinematic axes of the patient's knee. In one implementation, the system can derive the position of the transepicondylar axis of the knee and the mechanical axis of the femur and/or tibia of the patient. Additionally or alternatively, the system can derive the flexion-extension axis of the knee (e.g., by locating the geometric center of each femoral condyle and aligning the axis with these geometric centers). However, the system can derive the position, in 3D space, of any other axis useful for the placement of implants in total knee arthroplasty.

1.4 Tension Data Collection

Generally, in Blocks S120 and S122, the system can access tension data for the ligaments of a patient's knee (e.g., the MCL and the LCL of the patient) in order to calculate a soft tissue envelope for each of the patient's ligaments in the patient's knee joint. More specifically, the system can access tension data for the ligaments of the patient's knee throughout the range of motion of the patient's knee that was intraoperatively obtained by a surgeon via a particular tension measurement procedure. Furthermore, as shown by FIG. 2, the system can obtain dynamic tension data for the patient during articulation of the patient's knee through the range of motion multiple times, thereby collecting data representative of viscoelastic characteristics of the ligament. The system can then account for the range of intraoperative tensions experienced by the patient's ligament for a given extension length when calculating a range of target postoperative tensions for a patient's ligament.

Thus, the surgeon may begin a total knee arthroplasty by making an incision to expose the joint capsule of the patient's knee and the MCL and LCL of the patient. The surgeon may then attach or apply tension measuring devices or sensors while repeatedly articulating the patient's knee to obtain intraoperative "dynamic" tension data. Additionally, the surgeon may open the joint capsule of the knee of the patient in order to insert spacers between one or both of the patient's femoral condyles and the patient's tibial plateau in order to obtain tension data corresponding to a modified geometry of the patient's knee joint (e.g., to compensate for pathologically low ligament tensions due to bone loss within the joint). Furthermore, the surgeon may insert spacers of multiple thicknesses in order to obtain tension data for multiple spacings (e.g., in order to obtain tension data for differing articulation dynamics of the knee joint).

Additionally, the system can access pressure data indicating the contact pressure between each of the femoral condyles and the tibial plateau throughout articulation of the patient's knee in order to calculate a target postoperative pressure profile of the femoral component of an implant articulating on the tibial component of the implant.

Furthermore, the system can access trajectory data indicating the path, in 3D space, of a reference point in the patient's bony tissue during articulation of the patient's knee in order to calculate a target postoperative trajectory for the reference point. For example, the system can access data indicating the trajectory of the patella throughout articulation of the patient's knee.

The system can access the aforementioned dynamic tension data in any way based on the corresponding method of data storage. In one implementation, the system accesses the tension data from a database connected to the system via a local area network or wide area network such as the Internet. In another implementation, the system receives and stores the dynamic tension data during surgery as the data is recorded by surgical digital tension meters or other sensors operated by the surgeon that are electrically-coupled or wirelessly-connected to the system. In yet another implementation, the surgeon may enter a set of tension measurements from an analogue tension meter or other surgical instrument via the surgeon portal.

1.4.1 Discrete Tension Measurements

In one implementation, the system accesses dynamic tension data in the form of discrete tension measurements intraoperatively recorded by a surgeon. For example, a surgeon may obtain a series of measurements and record the articulation angle of the patient's knee and the tension of each ligament at that articulation angle. In another example, the surgeon can measure the tension of the patient's MCL and LCL at terminal extension (0°), early extension (10°), mid-flexion (45°), flexion (90°), and deep flexion (120°). Thus, the surgeon may record ten tension measurements, five for each ligament. However, the surgeon may record any other number of tension measurements corresponding to angles of articulation of the patient's knee.

1.4.2 Dynamic Tension and Motion Sensor Measurements

In one implementation, the system accesses dynamic tension data in the form of concurrent and/or repeated tension measurement and articulation measurements. In this implementation, the system is connected to an electronic tension meter to obtain tension measurements from one or both of the patient's MCL and LCL. Additionally, the system obtains concurrent measurements of the articulation angle of the patient's knee. Thus, the surgeon may place the tension meter on the patient's MCL and/or LCL and articulate the patient's knee through its full range of motion while the system records tension data from the tension meter associated with the concurrent angle of articulation of the patient's knee.

In one implementation, the system can detect (e.g., via an overhead camera or LIDAR system) the articulation angle of the knee in 3D space utilizing motion capture software and/or computer vision techniques. For example, the system can record successive timestamped images of the surgical field; calculate an angle of articulation for each of the successive images; and associate each calculated angle of articulation with a concurrent tension data point according to the timestamp of the image. Additionally, the surgeon may apply visual indicators to reference points on the patient's bony anatomy in order to facilitate the system's ability to detect the articulation angle of the patient's knee joint. For example, the surgeon can place a visual indicator at a reference position on the patient's distal femur and a second visual indicator at a second reference position on the patient's proximal tibia and the system can approximate an angle of articulation as the angle between the two reference positions about a kinematic axis of the knee.

In an alternative implementation, the surgeon can attach a set of inertial measurement units (hereinafter "IMUs") to the patient's femur and tibia in order to measure the angle of articulation of the patient's knee joint concurrent with the measurement of tension in each of the patient's ligaments (via an electronic tension meter).

In each of the above implementations, the system can generate a surgeon portal, via a screen in the operating room, an augmented reality interface, and/or implement a voice command, to allow the surgeon to input the approximate location of either the visual indicators or the IMUs on the patient relative to the patient-specific knee joint model. Thus, the system can approximate the articulation angle of the patient's knee joint by simulating articulation of the patient-specific knee joint model to best replicate the visual data or the IMU data.

1.4.3 Patellar Trajectory

In one implementation, the system can access patellar trajectory data indicating the trajectory of the patella in the trochlea. The surgeon may attach an IMU or other tracking device to the patella during surgery such that the system can detect the trajectory of the patella relative to the trochlea upon articulation of the patient's knee joint. Alternatively, the system can: record successive images of the surgical field as the surgeon articulates the knee joint of the patient; and, based on the successive images, detect a trajectory of the patella in the trochlea.

1.4.4 Simulation of Tension Measurements

In one implementation, the system can estimate tension according to a simulation of the patient's knee joint according to a patient-specific knee joint model. In one implementation, the system generates a patient-specific knee joint model based on preoperative scans and intraoperative imagery in order to estimate the relative position of the femoral and tibial entheses of the MCL and LCL of the patient based on the change in length of each ligament throughout articulation of the patient-specific knee joint model. Additionally or alternatively, the system can assign the elasticity and/or other physical properties of the ligament based on intraoperative tension data obtained by the surgeon. Thus, the system can extrapolate (via the above described physical simulation) a set of dynamic tension data from a single tension measurement obtained by a surgeon.

1.5 Target Tension and Ligament Length Estimation

After obtaining a set of dynamic tension data (i.e. tension data from each ligament associated with a concurrent articulation angle of the knee joint), from a patient's MCL and LCL over a range of articulation angles, the system can estimate a range of acceptable target tensions for each of the patient's ligaments. Generally, the system: calculates the length of the ligament at each articulation angle based on the anatomy of the patient (e.g., the patient-specific knee joint model); correlates the lengths of the ligament with the tension measured in the ligament throughout the articulation range of the patient's knee joint; identifies the late toe-in and linear portions of the ligament length versus tension curve wherein the ligament experiences plastic deformation (as shown in FIG. 2); and extracts the corresponding target tension range from the identified linear portion of the curve.

In one implementation, while the surgeon intraoperatively collects tension data from the patient's MCL and LCL, the system can visually locate (e.g., via computer vision techniques) each enthesis of the MCL or LCL of the patient in order to calculate the length of the MCL or LCL at each articulation angle of the patient's knee joint. Alternatively, the system can calculate the length of the patient's MCL and/or LCL of the patient by locating the MCL and or LCL in the patient-specific knee joint model based on the detected anatomy of the patient; simulating articulation of the patient-specific knee joint model; and extracting the length of the MCL and LCL from the model at each articulation angle of the knee.

Once the system has calculated the length of the patient's MCL and LCL associated with each tension data point, the system can correlate the tension in each ligament with the associated length and identify a linear portion of the tension-length curve. The system can identify the linear portion of the curve according to any mathematical method such as calculating the second derivative of the curve and identifying the portion of the second derivative of the curve substantially close to zero as being linear. Upon identifying the linear portion of the curve, the system can reference the tension-length curve to extract target tension range for the ligament.

In one implementation, if the system does not identify that any portion of the curve is linear and therefore the ligament is not exhibiting elastic deformation, then the system can designate the ligament as pathologic (e.g., pathologically loose or pathologically tight) and estimate a target tension of the ligament by extrapolating the tension-length curve and according to known material properties of human ligaments.

In another implementation, the system can identify initial tension imbalance between the ligaments based on the respective tension-length curves for the MCL and the LCL of the patient. For example, if the initial tension of the patient's MCL is predominantly within the target tension range (e.g., within the linear portion of the estimated tension-length curve for the MCL) while the initial tension for the patient's LCL is outside of the target tension range for the LCL (e.g., outside of the estimated linear portion of tension-length curve for the MCL), then the system can indicate the patient's LCL is pathologically imbalanced and can recommend reconstruction or partial resection of the ligament to improve postoperative joint stability. Generally, the system can recommend reconstruction of a ligament when the system detects that the ligament is exhibiting tension below the target tension for the ligament (defined by the linear portion of the estimated tension-length curve) and the system can recommend partial resection of a ligament when the ligament is exhibiting tension above the target tension for the ligament (e.g., experience plastic deformation upon articulation of the patient's knee joint through its full range of motion).

Figure 3A:
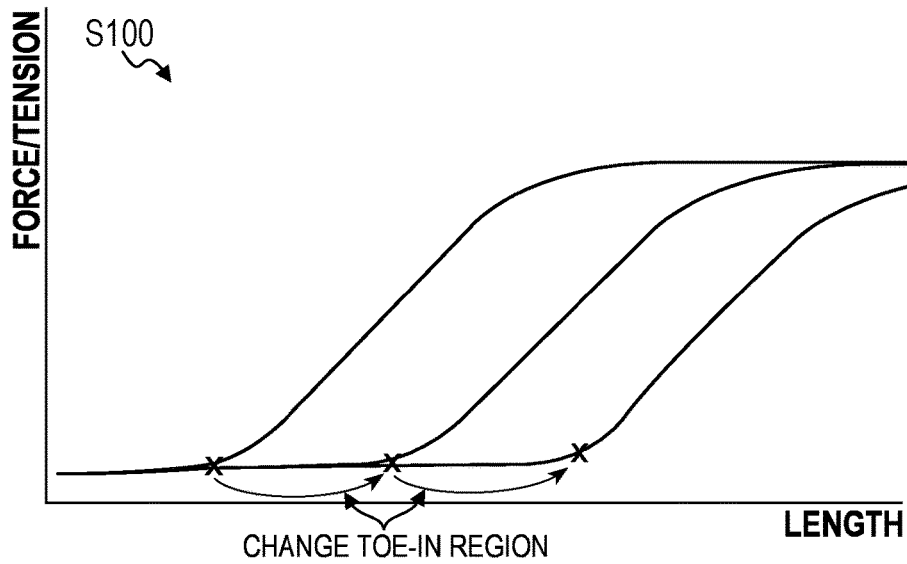
FIGS. 3A, 3B, and 3C are graphical representations of additional variations of the first method.
Figure 3B:
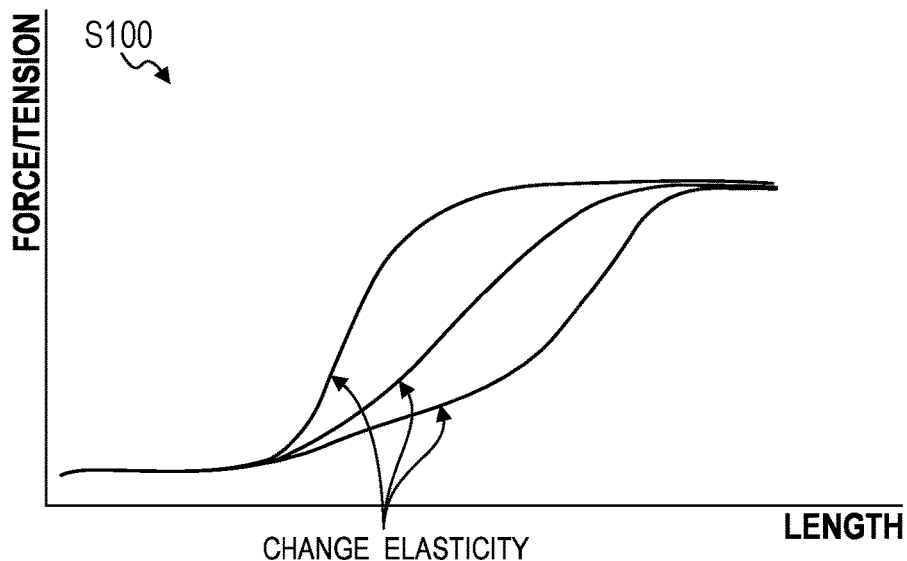
Figure 3C:
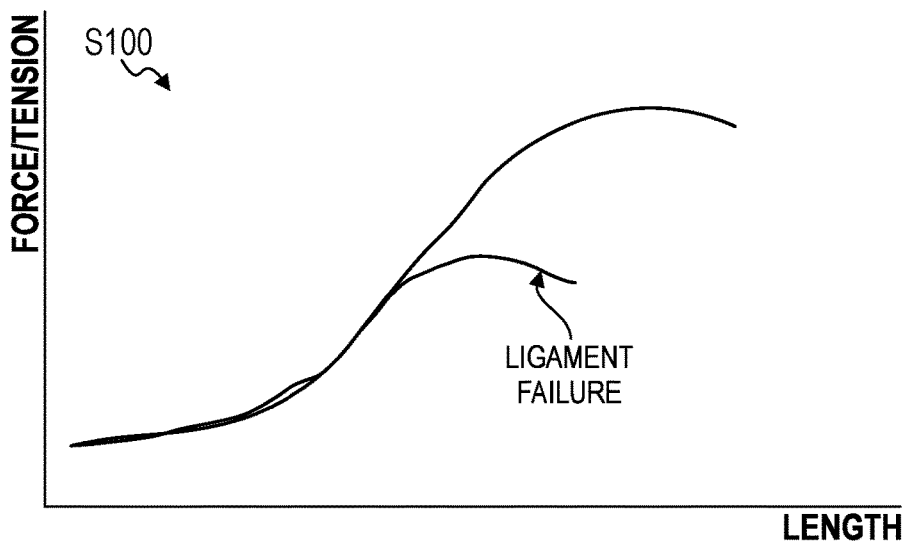

Furthermore, the system can calculate target tension by predicting a change in length of the toe-in region for a ligament, as shown in FIG. 3A. Additionally, the system can predict changes in elasticity of a ligament during surgery and account for these effects while calculating target tensions and ligament lengths for a ligament as shown in FIG. 3B. The system can also detect and account for ligament failure based on the ligament tension and adjust the target tensions and target ligament lengths accordingly as shown in FIG. 3C.

1.6 Soft Tissue Envelope Calculation

Generally, in Blocks S130 and S132, and as shown in FIG. 1, the system calculates a soft tissue envelope for each relevant ligament in the patient's knee joint (e.g., the patient's MCL and LCL). More specifically, the system can calculate lengths of the patient's MCL and LCL at which the patient's MCL and LCL are predicted to exhibit a tension within the target tension range in order to ensure better balance in the knee joint prosthesis, thereby improving postoperative implant durability and patient mobility. Thus, the soft tissue envelope can define a radial volume of space about a reference enthesis (e.g., the femoral enthesis or the tibial enthesis) of each ligament, which defines acceptable positions for the opposite enthesis of each ligament. For example, if the femoral enthesis of the patient's MCL is designated as the reference position, then the system would define a medial soft tissue envelope that indicates positions (e.g., in 3D space relative to the patient-specific knee joint model) of the tibial enthesis of the patient's MCL that result in an MCL length that corresponds to a tension within the target tension range.

1.7 Implant Designation

Generally, the system can access a model of an implant comprising a femoral component and a tibial component in Block S140 by first designating an implant for the patient. More specifically, the system can either selected an implant from a predetermined set of implants based on a best fit between the implant and the patient's bony anatomy and soft tissue envelopes, or the system can receive a designation of an implant from the surgeon via the surgeon portal.

1.7.1 Surgeon Implant Designation

In one implementation, the system can receive a designation of an implant for the patient from the surgeon via the surgeon portal. The system can display a list of a predetermined set of available implants to the surgeon via the surgeon portal and receive selection of an implant from the list of implants. Upon receiving selection of an implant via the surgeon portal, the system can retrieve a 3D model of the implant from an implant model database.

1.7.2 Implant Selection

In one implementation, the system can: designate or recommend an implant by selecting an implant that best fits the bony anatomy of the patient (e.g., the mechanical and/or kinematic axes of the patient's knee joint) and/or the soft tissue envelope of the patient; and access the model for the designated implant. The system can simulate the trajectory of the patient's tibia relative to the femur (or vice versa) according to the patient-specific knee joint model and overlay the mechanical and/or kinematic axes and the medial and lateral soft tissue envelopes defined by the patient's MCL and LCL respectively. The system can then virtually align each implant from a predetermined set of implants with the patient's anatomy and predict and postoperative trajectory of the patient's bony anatomy when modified by the implant. The trajectory of the bony anatomy also dictates the position of the entheses of the MCL and LCL. The system can then evaluate the extent to which the trajectory of the entheses of the MCL and the LCL coincides with the corresponding soft tissue envelope (e.g., the range of motion during which the enthesis coincides the soft tissue envelope). The system can then select an implant that has the greatest overlap between the trajectory of the entheses and the respective soft tissue envelopes of the MCL and LCL of the patient.

In implementations wherein the system recommends an implant from a predetermined list of implants, the system can display the recommendation to the surgeon via the surgeon portal and receive confirmation of the recommendation or selection of a different implant from the surgeon portal.

1.8 Surgical Guidance

Upon designation of the surgical component, in Block S150, the system can calculate a trajectory of a femoral cut relative to an axis of the femur, a placement of the femoral component, a trajectory of a tibial cut relative to an axis of the tibia, and the placement of a tibial component, based on the geometry of the distal femur, the geometry of the proximal tibia, the model of the implant, the medial soft tissue envelope, and the lateral soft tissue envelope. Generally, the system can define a surgical plan for a total knee replacement according to the designated implant, the patient's bony anatomy, and the soft tissue envelopes of the patient's MCL and LCL. Furthermore, the system can monitor the progression of the total knee replacement in real time and adjust subsequent steps of the surgical plan or recommend revision of previous steps based on deviations from the surgical plan.

The system can retrieve models for a femoral component, a tibial component, and/or a patellar component corresponding to the designated implant. Additionally, the system can retrieve models of a femoral cutoff jig, and/or a tibial cutoff jig. In this example, the system can then automatically place the femoral, tibial, and patellar components in target implant positions within the patient-specific knee joint model based on the mechanical and/or kinematic axes of the patient's femur and tibia. The system can subsequently modify the alignment of the target implant positions within acceptable anatomical tolerances such that the predicted trajectories of the entheses of the patient's MCL and LCL fall within the soft tissue envelope. The system can then serve the patient-specific knee joint model with the femoral component, the tibial component, and the patellar component positioned accordingly on the femur and tibia in the patient-specific knee joint model to the surgeon through the surgeon portal. The system can also determine target positions of the femoral and tibial cutoff jigs relative to the femur and tibia in the patient-specific knee joint model to achieve these initial femoral, tibial, and/or patellar component positions; and the system can serve the patient-specific knee joint model—with the femoral cutoff jig and the tibial cutoff jig in these target positions relative to the femur and to tibia—to the surgeon through the surgeon portal, as shown in FIG. 1.

Additionally or alternatively, the system can define target positions of cut planes relative to the femur and tibia in the patient-specific knee joint model to achieve bone removal sufficient to achieve these target femoral, tibial, and patellar component positions, as shown in FIG. 1. The system can similarly define cutting tool trajectories (e.g., "cut paths") relative to the femur and tibia in the patient-specific knee joint model that, when executed with a real surgical saw, yield bone removal sufficient to achieve the foregoing target femoral, tibial, and patellar component positions. The system can thus serve the patient-specific knee joint model—with the cut planes and/or with a cutting tool animated along the cutting tool trajectories in the patient-specific knee joint model—to the surgeon through the surgeon portal. The surgeon can then accept or modify these target positions of the artificial femoral component, the artificial tibial component, the artificial patellar component, the cut planes, and/or the cutting tool trajectories through the surgeon portal. The system can thus automatically construct a virtual surgical environment depicting virtual patient tissue and locating one or more virtual surgical objects relative to the virtual patient tissue.

The surgical plan can similarly define positions of a cut plane, a cut axis (e.g., a mechanical and/or kinematic axis of femur and/or the tibia), a surgical tool, a surgical tool trajectory, and/or any other surgical object relative to the patient-specific knee joint model. The system can therefore implement methods and techniques as described above: to locate a cut plane within the virtual surgical environment; to locate a surgical tool within the virtual surgical environment; or to locate any other virtual surgical object within the virtual surgical environment.

1.8.1 Femoral Resection

The system can initially indicate an orientation of a cut plane or trajectory relative to the patient's femur in the patient-specific knee joint model in order to enable placement of the femoral component of the designated implant by the surgeon at a target location. Thus, the system defines the femoral resection cut plane based on the target location of the femoral component of the designated implant.

The system can calculate an initial target position and orientation of the femoral cut plane based on standard alignment procedures of the implant according to the mechanical axis of the femur (e.g., 3 degrees valgus of the perpendicular mechanical axis) and at a depth specified according to the implant (e.g., 8 mm). Alternatively, the system can align the implant based on other axes such as the transepicondylar axis of the femur, the kinematic axis of the patient's knee, the flexion-extension axis of the patient's knee, the anatomical axis of the patient's femur, and/or the anatomical axis of the patient's tibia. Upon calculation of the initial position of the cut plane (and corresponding femoral component placement) the system can estimate a postoperative trajectory of the patient's MCL enthesis and LCL enthesis through articulation of the patient's knee and determine whether the trajectory aligns with the medial soft tissue envelope and the lateral soft tissue envelope respectively. The system can then modify the initial target position and orientation of the femoral cut plane and corresponding femoral component placement to better align with the medial soft tissue envelope and the lateral soft tissue envelope, thereby generating a balanced target position and orientation for the femoral cut plane.

In one implementation, the system can account for engineering tolerance in the implant in calculating alignment between the estimated postoperative trajectory of the patient's MCL enthesis and LCL enthesis and the medial and lateral soft tissue envelopes. In one example, the system can estimate multiple postoperative trajectories of the patient's MCL enthesis and LCL enthesis at the extremes of tibial component placements within the engineering tolerance of the designated implant.

1.8.2 Femoral Resection Correction

After the surgeon has performed resection of the femur according to the femoral cut plane/trajectory, the system can access an image and/or LIDAR scan of the surgical field to assess the actual cut plane/trajectory relative to the planned femoral cut plane/trajectory. Based on the observed actual cut plane/trajectory, the system can re-estimate the postoperative trajectory of the MCL enthesis and LCL enthesis given a placement of a femoral component consistent with the actual cut plane. If the system detects significant deviation in trajectory (e.g., the trajectory no longer coincides with the soft tissue envelope to the same degree), then the system can recommend revision of the femoral resection. If there are no significant imbalances caused by the deviation in the actual femoral cut plane, then the system can update the surgical plan to compensate for the deviation.

For example, the system can calculate an updated placement of the tibial cut plane and an updated placement of the tibial component to align with a femoral component placement corresponding to the actual femoral cut. Thus, any error in femoral resection is not carried forward to subsequent surgical steps.

1.8.3 Femoral Component Placement

Upon resection of the patient's femur, the system can update a planned femoral component placement according to deviations in the femoral resection performed by the surgeon. The system can calculate a femoral component placement that best approximates alignment with the relevant axis of the patient's femur (e.g., the mechanical, anatomical, and/or kinematic axes) and provides alignment of the predicted trajectory of the MCL enthesis and LCL enthesis of the patient within the medial and lateral soft tissue envelopes.

1.8.4 Femoral Component Correction

After the surgeon has placed the femoral component of the designated implant, the system accesses images and/or LIDAR scans of the surgical field in order to assess the actual placement of the femoral component compared to the planned placement of the femoral component. The system can then update subsequent steps of the surgical procedure to correct changes in alignment of the implant with the relevant axes of the femur and/or changes in the trajectory of the MCL and LCL entheses of the patient relative to the medial and lateral soft tissue envelopes.

1.8.5 Tibial Resection

The system can initially indicate an orientation of a tibial cut plane/trajectory relative to the patient's tibia in the patient-specific knee joint model in order to enable placement of the tibial component of the designated implant by the surgeon at a target location. Thus, the system defines the tibial resection cut plane based on the target location of the tibial component of the designated implant.

The system can calculate an initial target position and orientation of the tibial cut plane based on standard alignment procedures of the implant according to the mechanical axis of the femur (e.g., perpendicular to the mechanical axis of the tibia) and at a depth specified according to the implant (e.g., 9 mm below the tibial plateau). Alternatively, the system can calculate the tibial cut plane/trajectory based on the previous placement of the femoral component, the planned placement of the femoral component, and/or the actual location of the femoral cut. Upon calculation of the initial position of the tibial cut plane (and corresponding tibial component placement) the system can estimate a postoperative trajectory of the patient's MCL enthesis and LCL enthesis through articulation of the patient's knee and determine whether the trajectory aligns with the medial soft tissue envelope and the lateral soft tissue envelope respectively. The system can then modify the initial target position and orientation of the tibial cut plane and corresponding tibial component placement to better align with the medial soft tissue envelope and the lateral soft tissue envelope thereby generating a balanced target position and orientation for the tibial cut plane.

1.8.6 Tibial Resection Correction

Upon resection of the tibia by the surgeon, the system can access images and/or LIDAR scans of the surgical field to assess the actual cut plane/trajectory defining resection of the tibia compared to the planned cut plane/trajectory of the tibia. The system can then estimate the resulting change in the position of the tibial component based on the deviation between the actual resection of the tibia and the planned resection of the tibia. The system can then re-estimate articulation of the knee joint through the range of motion of the knee joint to obtain trajectories for the MCL enthesis and LCL enthesis of the patient given the new position of the tibial component derived from the deviation in the tibial resection. The system can then estimate whether a revision to the tibial resection (e.g., further resection of the tibia) is recommended to maintain balanced postoperative tension in the MCL and LCL of the patient. Alternatively, the system can prompt the surgeon to add a spacer between the tibial component and the resected surface of the tibia to correct the deviation of the tibial resection from the planned tibial resection. Furthermore, the system can update the planned tibial component placement according to the actual tibial resection in order to compensate for deviations between the actual tibial resection and the planned tibial resection.

1.8.7 Tibial Component Placement

Upon resection of the patient's tibia by the surgeon, the system can update a planned femoral component placement according to deviations in the tibial resection performed by the surgeon when compared to the planned tibial resection. The system can then calculate a tibial component placement that best approximates alignment with the relevant axis of the patient's tibia (e.g., the mechanical, anatomical, and/or kinematic axes) and provides alignment of the predicted trajectory of the MCL enthesis and LCL enthesis of the patient within the medial and lateral soft tissue envelopes.

1.8.8 Tibial Component Correction

After the surgeon has placed the femoral component of the designated implant, the system accesses images and/or LIDAR scans of the surgical field in order to assess the actual placement of the tibial component compared to the planned placement of the tibial component. The system can then predict/simulate the alignment of the implant relative to the axes of the patient's knee and the trajectories of the MCL enthesis and the LCL enthesis relative to the medial and lateral soft tissue envelopes based on the actual placement of the tibial component. The system can then recommend revision of the tibial component placement or introduction of a spacer between the tibial component and the resected tibial surface in order to improve alignment and or the trajectory of the enthesis within the soft tissue envelope.

1.9 Tension Check and Revision

Upon completion of the tibial component placement by the surgeon and subsequent mechanical engagement of the tibial component with the femoral component, the system can access a second set of intraoperative tension data to evaluate the tension in the MCL and the LCL of the patient and can prompt the surgeon to revise prior surgical steps and/or modify the patient's MCL and LCL. Therefore, the surgeon can perform similar tension data collection steps to those described with respect to the initial intraoperative tension data collection.

After accessing a second set of tension data collected by the surgeon, the system can compare the second set of tension data for each ligament (e.g., the patient's MCL and LCL) to the target postoperative tension of the ligament. In response to detecting a deviation between the target post-operative tension of a ligament and the tension exhibited by the ligament according to the second set of tension data, the system can prompt the surgeon to correct the deviation.

In one implementation, in response to detecting a lower than target tension in a ligament, the system can prompt the user to install a shim or spacer between the tibial component and the tibia of the patient, thereby increasing tension in the ligaments. Alternatively, in response to detecting a higher than target tension in a ligament, the system can prompt the surgeon to remove a shim or space between the tibial component and the tibia of the patient or installing a lower profile tibial component, thereby reducing tension in a ligament. Furthermore, in response to detecting a tension imbalance between the MCL and the LCL of the patient (e.g., the patient's MCL exhibits a higher than target tension while the patient's LCL exhibits a lower than target tension or vice versa), the system can prompt the surgeon to install an uneven spacer or tibial component that corrects the tension imbalance within the engineering tolerance of the designated implant and the alignment constraints of the implant relative to the mechanical and/or kinematic axes of the knee joint of the patient.

2. Second Method

Figure 4:
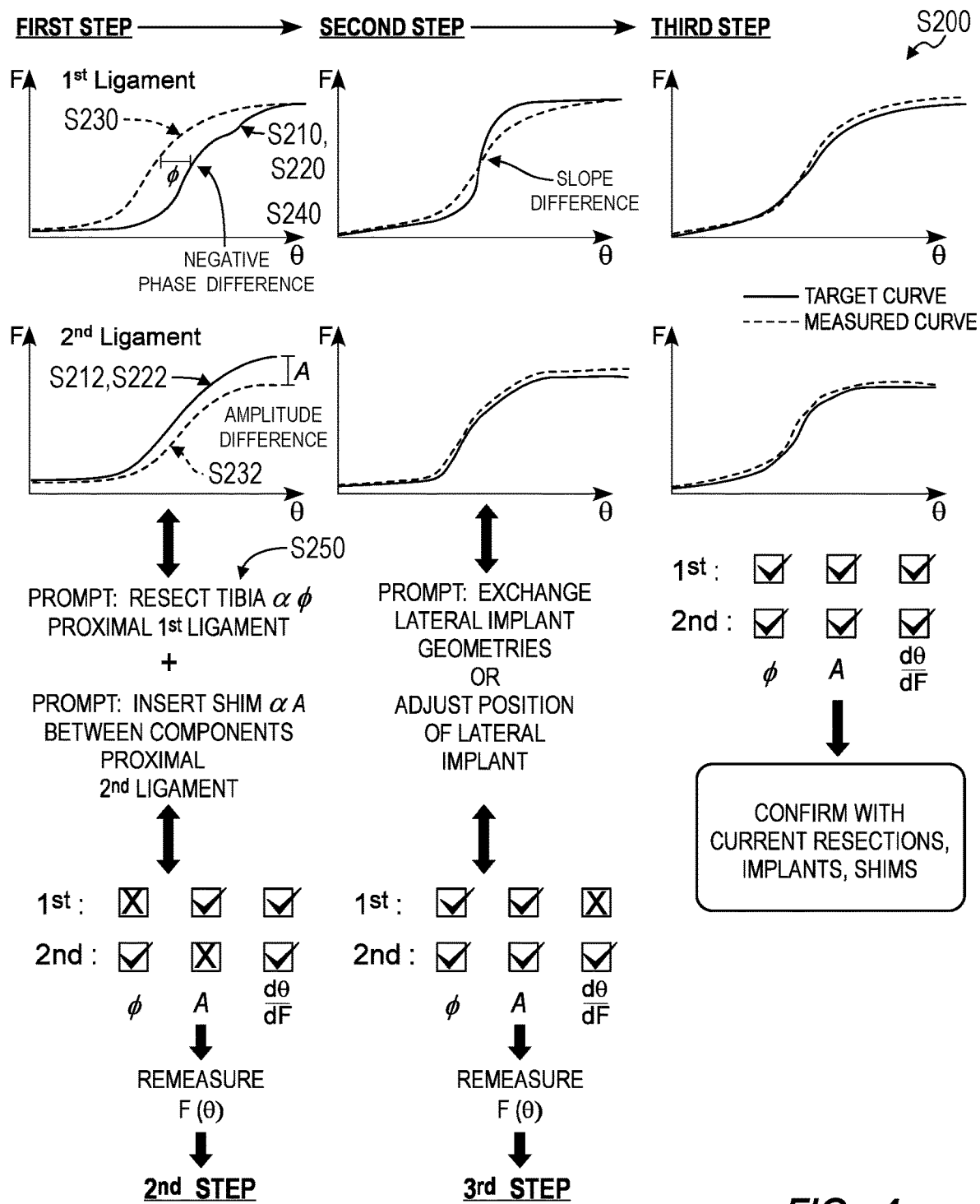
FIG. 4 is a flowchart representation of a second method.

As shown in FIG. 4, a second method S200 for generating intraoperative surgical guidance during a total knee arthroplasty includes: at a first time, preceding resection of a first bone and a second bone in a knee of a patient: generating a first ligament tension curve for a first ligament in the knee at Block S210; generating a second ligament tension curve for a second ligament in the knee at Block S212; storing a first target tension curve for the first ligament based on the first ligament tension curve at Block S220; and storing a second target tension curve for the second ligament based on the second ligament tension curve at Block S222; and, at a second time, succeeding resection of the first bone and succeeding placement of a first test implant on the first bone: generating a third ligament tension curve for the first ligament at Block S230; generating a fourth ligament tension curve for the second ligament at Block S232; characterizing a first phase difference between the third ligament tension curve and the first target tension curve at Block S240; characterizing a second phase difference between the fourth ligament tension curve and the second target tension curve at Block S242; and in response to the first phase difference exceeding a threshold negative phase difference, outputting a first prompt to a surgeon to further resect the first bone proportional to the first phase difference at Block S250.

2.1 Applications

Generally, the second method S200 can be executed by the system (e.g., in conjunction with and/or in place of Blocks of the first method S100) during a total knee arthroplasty procedure in order to: sample and/or access preoperative tension characteristics of ligaments within the knee; and identify target post-operative ligament tension characteristics based on the sampled preoperative tension characteristics. Following initial tibial and femoral cuts and placement of temporary test tibial and femoral components, the system can: sample and/or access intraoperative tension data for each ligament within the knee; characterize deviations and/or differences between these intraoperative tension data and target tension characteristics; and recommend a set and/or sequence of remedial steps to the surgeon—such as placement of different test components of a different geometry on the bone, further resection of the femur and/or tibia to enable different placements of these test components, installation of final femoral and tibial components, or insertion of a spacer between the final femoral and tibial components—predicted to correct and/or ameliorate these deviations. Thus, the system can generate a dynamic, multi-step surgical plan and/or dynamic surgical guidance based on sampled intraoperative ligament tension data during a knee arthroplasty procedure in order to: maintain or improve post-operative ligament tension characteristics for individual ligaments within the knee; maintain or synchronize ligament tension balance across multiple ligaments within the knee; reduce and/or eliminate a need to resect or release any of these ligaments during the surgery; and thus increase probability of a positive outcome for the patient and reduce patent recovery time.

More specifically, the system can: sample and/or access pre-operative tension data for each ligament within the knee as the knee is articulated (e.g., by the surgeon) through its full range of motion; transform these pre-operative tension data into baseline ligament tension curves (e.g., stress-strain curves) representing displacement of the ligament (e.g., as measured by length of the ligament, angular displacement of the knee etc.) as a function of force applied to the ligament (e.g., tension in the ligament) throughout articulation of the knee; and store the baseline ligament tension curves as a set of target tension characteristics. The system can then calculate a set of bone resection parameters (e.g., resection angles and resection distances of the femur and tibia) and identify femoral and tibial implant geometries predicted to most closely achieve the set of target tension characteristics. Alternatively, the system can detect and characterize (e.g., via optical and/or LIDAR images of the surgical site) parameters of bone resections already performed by the surgeon and/or geometries of implant components selected by the surgeon (e.g., as initial baseline steps in the arthroplasty procedure). Upon remeasuring intraoperative ligament tension curves (e.g., following bone resection and temporary insertion of test implant components), the system can identify deviations from the target tension characteristics according to phase, shape (e.g., slope), and/or amplitude (e.g., maximum value) differences between the intraoperative and baseline ligament tension curves. In response to detecting these differences, the system can generate a set or sequence of corrective steps based on: the type and/or magnitude of deviation; effects of these possible corrective steps on ligament tension characteristics predicted by bio-mechanical models of the knee and/or outcomes of previous procedures; difficulty of the possible corrective steps (e.g., probability of successful completion of the corrective step by the surgeon); and invasiveness and/or reversibility of these possible corrective steps. The system can then present this set or sequence of corrective steps to the surgeon, such as in the form of surgical options presented on a standalone display (e.g., a monitor), rendered via an augmented reality headset worn by the surgeon, or communicated to the surgeon via audible prompts.

By repeating this process during or following each step of the surgery, the system can regularly: re-characterize tension of ligaments in the joint; quantify the effects of actions taken and/or decisions made by the surgeon during the surgery; validate predictions and recommendations generated by the system against intraoperative ligament tension measurements recorded after these recommendations are executed (or deferred) by the surgeon; and converge on a bone resection geometry, implant characteristics, and an implant position predicted to yield post-operative ligament tension nearest the target tension characteristics. In particular, for each step of the surgery, the system can generate a set of resection, implant geometry, and implant position-related recommendations predicted to preserve a greatest scope of resection, implant geometry, and implant position-related options for future steps of the surgery in order to maintain a high probability of achieving the target tension characteristics upon conclusion of the surgery. The system can thus present these actionable recommendations to the surgeon during each step of the surgery, thereby enabling the surgeon to apply her expertise to elect and execute surgical decisions during individual steps of the surgery while also maintaining a high probability that the final tendon tensions over a range of motion of the joint with approximately the target tension characteristics set for the arthroplasty, thereby reducing post-operative pain and recovery time for the patient and improving joint comfort for the patient.

The second method S200 is described herein as executed by the system (e.g., a handheld computing device, a local or remote computer system, a computer network) to generate intraoperative surgical guidance to a surgeon during a knee arthroplasty (e.g., a total knee arthroplasty) based on observed and/or predicted effects of particular surgical steps on dynamics and mechanics of ligaments (e.g., the ACL, MCL, LCL, and PCL) within a patient's knee. However, the second method S200 and/or variations of the second method S200 can also be implemented by the system or other device during other arthroplasty procedures—such as a total hip arthroplasty, a shoulder surgery, or an ankle surgery—to monitor and predict effects of surgical steps based on target tissue tension characteristics and/or target joint range of motion characteristics and to generate intraoperative surgical guidance accordingly.

2.2 Terms

Figure 5:
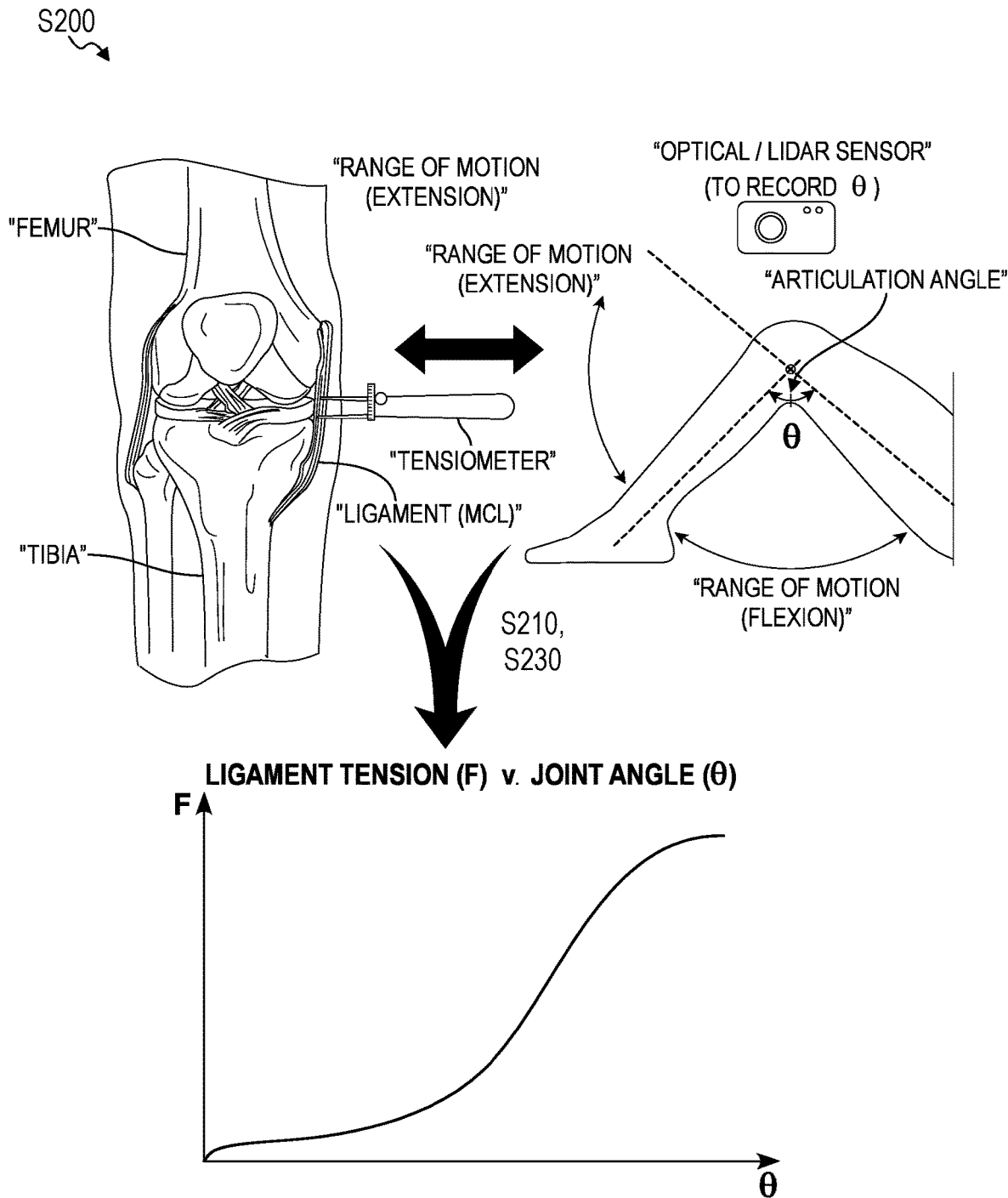
FIG. 5 is a flowchart representation of the second method.

The term "ligament tension curve" is referred to herein as a continuous curve or plot representing the tension (e.g., force) on a ligament within a joint (e.g., a knee) as a function of the length of the ligament (which is a function of angle of the joint) or as a function of the angle of the joint more generally. For example, the system can generate a ligament tension curve by fusing a ligament tension timeseries—measured by a tensiometer in contact with a ligament—and a joint angle timeseries—recorded by a contact-based position sensor arranged on each side of the joint or extracted from a video of the joint—as the joint is articulated through its range of motion, as shown in FIG. 5. As shown in FIG. 2, a ligament tension curve generally defines: a "toe-in region" at low displacements, in which the ligament experiences little or no increase in force or tension as the displacement of the ligament increases; a "linear region" at medium displacements, in which the force or tension on the ligament is directly proportional to the displacement of the ligament.

A "phase difference" between two ligament tension curves is referred to herein as a horizontal offset between the two ligament tension curves such that the linear region and/or the plastic deformation region of these ligament tension curves occur at different ligament displacements (e.g., or occur over different displacement intervals). For example, the phase difference between a first ligament tension curve and a second is described herein as a "negative phase difference" between a first ligament tension curve and a corresponding target ligament tension curve if the first ligament tension curve transitions to the linear region at a lower displacement (i.e., at a lower joint angle) than the linear portion of the corresponding target ligament tension curve.

The term "threshold phase difference" is referred to herein as a maximum phase difference—set, defined, and/or calculated by the system or entered by a surgeon—between a target ligament tension curve for a ligament and an actual ligament tension curve of this ligament measured during a surgery. In particular, the system can interpret the phase of a first ligament tension curve of a ligament as matching and/or within tolerance of a corresponding target tension curve of this ligament if the phase difference between the first and target tension curves is less than or equal to the threshold phase difference.

A "slope difference" between two ligament tension curves is referred to herein as a difference between the slope (i.e., change in force or tension on the ligament per unit displacement) of the linear region of the first ligament tension curve of a ligament and the slope of the linear region of the corresponding target ligament tension curve of the ligament.

The term "threshold slope difference" is referred to herein as a maximum slope difference—such as set, defined, and/or calculated by the system or entered by the surgeon—between a target ligament tension curve for a ligament and an actual ligament tension curve of this ligament measured during a surgery. In particular, the system can interpret the slope of a first ligament tension curve of a ligament as matching and/or within tolerance of the slope of a corresponding target ligament tension curve of this ligament if the slope difference between the first ligament tension curve and the target ligament tension curve is less than or equal to the threshold slope difference.

An "amplitude difference" between two ligament tension curves is referred to herein as a difference between a first global maximum force or tension value within the first ligament tension curve and a target global maximum force or tension value within the corresponding target ligament tension curve for a ligament. Thus, a "negative amplitude difference" between a first ligament tension curve and corresponding target ligament tension curve is referred to herein as an amplitude difference in which the maximum force or tension value represented in the first ligament tension curve is less than the maximum force or tension value represented in the corresponding target ligament tension curve for a ligament. Similarly, a "positive amplitude difference" between a first ligament tension curve and second ligament tension curve is referred to herein as an amplitude difference in which the maximum force or tension value represented in the first ligament tension curve is greater than the maximum force or tension value represented in the corresponding target ligament tension curve for a ligament.

The term "threshold amplitude difference" is referred to herein as a maximum amplitude difference—set, defined, or calculated by the system or entered by the surgeon—between a target global maximum force or tension value represented in a target ligament tension curve for a ligament and an actual maximum force or tension value of this ligament measured during a surgery. In particular, the system can interpret the amplitude of a first ligament tension curve of a ligament as matching and/or within tolerance of the amplitude of a corresponding target ligament tension curve of the ligament if the amplitude difference between the first ligament tension curve and the corresponding target ligament tension curve is less than or equal to the threshold amplitude difference.

The term "bone resection parameter" is referred to herein as an orientation, a position, an angle, and/or a resection depth (or resection distance) of a cut plane, a cut axis, or a cut trajectory on or relative to a bone structure (e.g., a femur or a tibia).

2.3 Examples

Generally, the system can execute Blocks of the second method S200 to provide guidance to a surgeon during a knee arthroplasty procedure (e.g., a total knee arthroplasty, a partial knee arthroplasty) by identifying and notifying the surgeon of a set of available corrective and/or predictive options at each step of the surgery in order to identify, or at least approximate, a set of implant characteristics and/or geometries best suited to the particular mechanics of the patient's knee, as indicated, for example, by pre-operative and intraoperative ligament tension characteristics.

Prior to initiating resecting bony tissue (e.g., femoral and tibial condyles) during the surgery, the system can sample and/or record preoperative ligament tension for a set of ligaments within the knee (e.g., the ACL, the MCL, the PCL, the LCL). For example, the system can prompt the surgeon to temporarily insert a force sensor (e.g., a tensiometer) into the knee of the patient in contact with each ligament and articulate the knee through a full range of natural motion. For each ligament, the system can concurrently: access and/or record a time series of angular positions of the knee during articulation of the knee via an angular position sensor (e.g., an angular position sensor placed within the knee, an imaging system arranged remotely from the knee); transform the first time series of angular positions into a time series of lengths of the ligament throughout articulation of the knee; access and/or record a time series of forces on the ligament during articulation of the knee via the force sensor; and compile the time series of forces on the ligament and the time series of lengths of the ligament into a preoperative ligament tension curve. The system can then derive target tension characteristics for each ligament based on the corresponding preoperative ligament tension curve. For example, in response to detecting that a particular preoperative ligament tension curve indicates healthy ligament dynamics, the system can store the preoperative ligament tension as a target tension characteristic for the corresponding ligament. Additionally and/or alternatively, in response to detecting that a particular preoperative ligament tension curve indicates a ligament pathology (e.g., the ligament is pathologically loose or pathologically tight during flexion or extension of the knee), the system can store a modified ligament tension curve, based on the sampled ligament curve, as the target tension characteristic and/or recommend remedial steps during the arthroplasty procedure to correct the detected ligament pathology.

As an initial step in the knee arthroplasty procedure, the system can characterize a bony anatomy of the patient, as described above (e.g., a relative angle of the femur and tibia, geometries of the patient's femoral and/or tibial condyles); and, for example, calculate an initial (e.g., baseline) set of bone resection parameters (e.g., cut angles, resection distances) for the tibia and/or femur based on target ligament tension characteristics, according to the bony anatomy of the patient and/or in accordance with a kit of available of femoral/tibial implant geometries. The system can then prompt the surgeon to resect the femur and/or tibia of the patient according to the initial set of bone resection parameters. Alternatively, the system can prompt the surgeon to resect the tibia and/or femur according to any (e.g., arbitrary) bone resection parameters and subsequently characterize resections performed by the surgeon.

Following resection of the tibia and/or femur, the system can prompt the surgeon to insert (e.g., temporary) test implants into the tibia and/or the femur and remeasure tension characteristics of each ligament. In one example, the system can access models (e.g., 3D models) of a kit of available implant geometries and select and/or recommend a particular implant geometry for the test implant based on characterized bone resection parameters and predicted effects on ligament tensions. In another example, the system can prompt the surgeon to insert a test implant of any available implant geometry (e.g., an arbitrary implant geometry). The system can then implement similar methods and techniques as described above to generate intraoperative tension curves for each ligament within the knee, thereby enabling the system to characterize the effects of the instant bone resection parameters and implant geometries on the patient's ligament dynamics.

As shown in FIG. 4, the system can then calculate existing deviations between each intraoperative tension curve and the target tension characteristics for the corresponding ligament and identify a set and/or sequence of possible remedial or proactive surgical steps predicted to more closely align observed ligament dynamics with the target tension characteristics based on generic and/or patient-specific biomechanical models of the knee and/or data recorded during previous procedures. In one example, the system can identify a phase difference between the intraoperative tension curve of a particular ligament and a target tension curve associated with the particular ligament, which may indicate that the target ligament goes into tension (e.g., elastic deformation) too early or too late during articulation of the knee (e.g., from flexion to extension). Thus, in response to detecting a negative phase difference (e.g., exceeding a threshold negative phase difference) between the intraoperative and target ligament tension curves, the system can calculate a set of parameters for additional resection of the femur and/or tibia predicted to widen a gap between the femoral and tibial implant components and thereby delay elastic deformation of the ligament during articulation of the knee. Alternatively, in response to detecting a positive phase difference between the intraoperative and target ligament tension curves, the system can calculate dimensions of a spacer and/or shim component for installation between the femoral and tibial implant components.

In another example, the system can identify a difference in shape and/or slope between the intraoperative tension curve and the target tension curve for a particular ligament, which may indicate that the current implant geometry and/or position of the test implant relative to the bone is incompatible with the bony anatomy of the patient and/or current bone resection parameters. Thus, in response to detecting a slope and/or shape difference between the intraoperative and target tension curves (e.g., exceeding a threshold slope difference), the system can: access models (e.g., 3D models) of femoral and/or tibial implants in a kit of implant geometries available during the surgery; predict the effect of each implant geometry on dynamics and/or tension characteristics of the ligament; select a particular implant geometry predicted to reduce or eliminate the detected slope/shape difference; and prompt the surgeon to exchange the test implant with a second test implant of the selected implant geometry.

In yet another example, the system can identify a difference in amplitude (or maximum value/maximum tension) between the intraoperative tension curve and the target tension curve, which may indicate that the ligament exhibits too much (or too little) tension within a particular range of articulation angles. Thus, in response to detecting a negative amplitude difference between the intraoperative tension curve and the target tension curve, the system can calculate dimensions of a spacer and/or shim component for installation between the femoral and tibial implant components, predicted to increase tension on the ligament throughout the particular range of articulation angles, based on the difference in amplitude between intraoperative tension curves and the target tension curves and the implant geometries of the currently placed test implants. For example, in response to detecting a negative amplitude difference between a first intraoperative tension curve for a first ligament on a lateral side of the knee, the system can: calculate a height for a lateral side of a spacer that is (e.g., directly) proportional to the negative amplitude difference and complements the currently installed test implant geometries; select a spacer geometry from a kit of spacers available during the surgery that is most closely analogous to the calculated spacer dimensions; and prompt the surgeon to install a spacer of the selected spacer geometry between the test femoral and tibial implant components. Alternatively, in response to detecting a positive amplitude difference between the intraoperative tension curve and the target tension curve, the system can recommend resection, release, and/or reconstruction of the corresponding ligament.

In the above examples, the system can set (e.g., calculate, derive) a maximum permitted deviation from the target tension characteristics—such as a threshold phase difference, a threshold amplitude difference, and/or a threshold slope difference based on the current surgical parameters (e.g., bone resection parameters, the bony anatomy of the patient) and tools known by the system to be available to the surgeon (e.g., the kit of available implant geometries, a range of available shim heights) in order to filter and/or customize recommended steps according to achievable outcomes of the surgery. For example, for a surgery in which the femur and/or tibia have been minimally resected (e.g., there exists an option to resect additional bone) and in which the kit of implant geometries available to the surgeon is large and/or diverse, the system can detect (e.g., calculate, identify) a high probability (e.g., confidence) of achieving a low slope difference between intraoperatively measured ligament curves and the target ligament tension curves. The system can then set or define a small threshold slope difference (e.g., a tighter tolerance for slope differences between intraoperative and target tension curves) for this surgery. Alternatively, for surgeries in which the kit of available implant geometries is small and/or limited, the system can set or define a larger threshold slope difference (e.g., tolerance). In another example, the system can set, calculate and/or define the threshold amplitude difference (e.g., amplitude tolerance) according to current bone resection parameters, available implant geometries and/or the range of spacer geometries available to the surgeon. For example, the system can set a small threshold amplitude difference (e.g., a tight amplitude tolerance) for a surgery in which the femur and tibia have been minimally resected during the initial cut and the surgeon has access to a large range of available spacer heights.

Generally, the system is also configured to predict the effects of a particular decision or step—such as additional resection of bone, exchanging two implant components, or insertion of spacer between implant components—on each ligament characterized during the surgery. Thus, while the system can identify a particular surgical step, set of steps, or sequence of steps predicted to correct detected deviations between a sampled intraoperative tension curves and a target tension curves (e.g., target tension characteristics) for a particular ligament, the system can generally exclude or deprioritize steps predicted to have a large (negative) effect on tension characteristics of other ligaments within the knee. Similarly, the system can exclude steps after which no other possible steps can (e.g., are predicted) realign intraoperative ligament tension characteristics with the target ligament tension characteristics. Finally, the system can exclude and/or deprioritize steps that are overly invasive and/or cannot be reversed during subsequent steps of the surgery, such as ligament resection or excessive bone resection. Therefore, the system can: rank, order and/or weight possible next steps in the surgical procedure according to the type and/or magnitude of deviation, effects of these possible corrective steps on ligament tension characteristics predicted by biomechanical models of the knee and/or outcomes of previous procedures, difficulty of the possible corrective steps (e.g., probability of successful completion of the corrective step by the surgeon), and invasiveness and/or reversibility of these possible corrective steps; and output a prompt to the surgeon to execute a particular step, set of steps, or sequence of steps according to this ranking/ordering/weighting—such as exchanging the one or more test implants for other test implants of a different geometry, inserting a spacer of a particular height and/or slope between two implants or resecting additional bone according to a calculated set of additional resection parameters.

Following execution of the recommended step(s) by the surgeon, the system can repeat the above methods and techniques to remeasure additional intraoperative tension curves for each ligament. The system can then update a (patient-specific) biomechanical model of the knee according to observed differences in ligament tension characteristics effected by the execution of the recommended step(s). In response to detecting that each additional intraoperative tension curve is analogous to the corresponding target tension (e.g., within a threshold tolerance), or in accordance with a determination that no further steps effect the target tension characteristics, the system can confirm the surgical plan according to current parameters and prompt the surgeon to (e.g., permanently) install corresponding components. Alternatively, in response to detecting additional deviations between intraoperative tension curves and the target tension characteristics for the corresponding ligaments, the system can repeat the above methods and techniques to identify a second set and/or sequence of remedial or proactive steps predicted to more closely align observed ligament dynamics with the target tension characteristics based effects of previously executed steps (e.g., as detected by the system), and/or the (updated) patient-specific biomechanical model of the knee and prompt the surgeon to execute these steps. The system can repeat this process in an iterative fashion until detecting that each additional intraoperative tension curve is analogous to the corresponding target tension (e.g., within a threshold tolerance), or until determining that no further steps effect the target tension characteristics.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

I claim:

1. A method for generating intraoperative surgical guidance during a knee arthroplasty, comprising:
by a computer system at a first time preceding resection of a first bone and a second bone in a knee of a patient:
accessing a first set of angular positions of the knee, output by an angular position sensor coupled to the knee, during articulation of the knee within a first test period;
transforming the first set of angular positions into a first set of lengths of a first ligament during articulation of the knee within the first test period;
accessing a first set of forces on the first ligament, output by a force sensor inserted into the knee proximal the first ligament, during articulation of the knee within the first test period; and
generating a first ligament tension curve for the first ligament in the knee based on the first set of forces on the first ligament and the first set of lengths of the first ligament;
generating a second ligament tension curve for a second ligament in the knee;
storing a first target tension curve, representing a first target postoperative relationship between tensions on the first ligament and lengths of the first ligament over the first set of angular positions of the knee, based on the first ligament tension curve; and
storing a second target tension curve, representing a second target postoperative relationship between tensions on the second ligament and lengths of the second ligament over the first set of angular positions of the knee, based on the second ligament tension curve; and
by the computer system at a second time succeeding resection of the first bone and succeeding placement of a first test implant on the first bone:
accessing a first interoperative set of angular positions of the knee, output by the angular position sensor coupled to the knee, during articulation of the knee within an interoperative test period;
transforming the first interoperative set of angular positions into a first interoperative set of lengths of the first ligament during articulation of the knee within the interoperative test period;
accessing a first interoperative set of forces on the first ligament, output by the force sensor inserted into the knee proximal the first ligament, during articulation of the knee within the interoperative test period; and
generating a third ligament tension curve representing an interoperative relationship between tensions on the first ligament and lengths of the first ligament over the first set of angular positions of the knee resulting from placement of the first test implant on the first bone;
generating a fourth ligament tension curve for the second ligament;
calculating a first phase offset between the third ligament tension curve and the first target tension curve;
calculating a second phase offset between the fourth ligament tension curve and the second target tension curve; and
in response to the first phase offset exceeding a threshold negative phase offset:
transforming the first phase offset into a first resection difference; and
rendering a first prompt, on a display, to further resect the first bone, proximal the first ligament, by the first resection difference.

2. The method of claim 1, further comprising:
accessing models of a kit of available implant geometries, the first test implant defining a first implant geometry in the kit of available implant geometries;
accessing models of a kit of available spacer geometries; and
calculating the threshold negative phase offset based on the kit of available implant geometries and the kit of available spacer geometries.

3. The method of claim 1, wherein outputting the first prompt comprises, in response to the first phase offset exceeding the threshold negative phase offset and in response to the second phase offset falling below the threshold negative phase offset, outputting generating the first prompt to further resect a first side of the first bone proximal the first ligament and to withhold further resection of a second side of the first bone proximal the second ligament.

4. The method of claim 1, further comprising:
at a third time succeeding the second time and succeeding further resection of the first bone:
generating a fifth ligament tension curve for the first ligament;
generating a sixth ligament tension curve for the second ligament;
calculating a third phase offset between the fifth ligament tension curve and the first target tension curve; and
calculating a fourth phase offset between the sixth ligament tension curve and the second target tension curve; and
in response to the third phase offset and the fourth phase offset falling within the threshold negative phase, offset:
validating resection of the first bone according to the target tension curve; and rendering confirmation, on the display, to progress to a next phase of the knee arthroplasty.

5. The method of claim 4, further comprising:
calculating a first slope difference between the fifth ligament tension curve and the first target tension curve;
calculating a first amplitude difference between the fifth ligament tension curve and the first target tension curve;
calculating a second slope difference between the sixth ligament tension curve and the second target tension curve;
calculating a second amplitude difference between the sixth ligament tension curve and the second target tension curve;
accessing models of a kit of available spacer geometries;
in response to the first amplitude difference exceeding a threshold amplitude difference:
 selecting a first spacer geometry defining a first spacer height from the kit of available spacer geometries based on the first amplitude difference, a first implant geometry of the first test implant, and the current set of bone resection parameters; and
 outputting a second prompt to the surgeon to insert a spacer of the first spacer geometry between the first test implant and the second bone proximal the first ligament; and
in response to the first slope difference exceeding a threshold slope difference:
 accessing models of a kit of available implant geometries;
 selecting a second implant geometry from the kit of available implant geometries based on the first slope difference, a first implant geometry of the first test implant, and the current set of bone resection parameters; and
 rendering a third prompt, on the display, to exchange the first test implant for a second test implant defining the second implant geometry.

6. The method of claim 1, wherein generating the second ligament tension curve comprises:
accessing a second time series of angular positions of the knee, output by the angular position sensor coupled to the knee, during articulation of the knee within the first test period;
transforming the second time series of angular positions into a second time series of lengths of the second ligament during articulation of the knee during the first test period;
accessing a second time series of forces on the second ligament, output by the force sensor temporarily inserted into the knee proximal the second ligament, during articulation of the knee within the first test period; and
compiling the second time series of forces on the second ligament and the second time series of lengths of the second ligament into the second ligament tension curve.

7. The method of claim 1, further comprising:
accessing models of a kit of available implant geometries;
characterizing a first slope difference between the third ligament tension curve and the first target tension curve;
characterizing a second slope difference between the fourth ligament tension curve and the second target tension curve; and
in response to the first slope difference exceeding a threshold slope difference:
 selecting a second implant geometry, from the kit of available implant geometries, based on the first slope difference and a first implant geometry of the first test implant; and
 rendering a second prompt, on the display, to exchange the first test implant for a second test implant of the second implant geometry.

8. The method of claim 7, further comprising calculating the threshold slope difference based on the kit of available implant geometries, a kit of available spacer geometries, and a set of bone resection parameters corresponding to resection of the first bone.

9. The method of claim 7, wherein selecting the second implant geometry comprises, in response to the second slope difference falling below the threshold slope difference, selecting the second implant geometry, from the kit of available implant geometries that is:
dissimilar to the first implant geometry adjacent a first side of the first bone proximal the first ligament; and
analogous to the first implant geometry adjacent a second side of the first bone proximal the second ligament.

10. The method of claim 7, further comprising:
at a third time succeeding the second time and succeeding exchange of the first test implant for the second test implant:
 generating a fifth ligament tension curve for the first ligament;
 generating a sixth ligament tension curve for the second ligament;
 calculating a third slope difference between the fifth ligament tension curve and the first target tension curve;
 calculating a fourth slope difference between the sixth ligament tension curve and the second target tension curve; and
in response to the third slope difference and the fourth slope difference falling within a threshold slope difference:
 confirming the second implant geometry; and
 rendering confirmation, on the display, of the second implant geometry.

11. The method of claim 10, further comprising:
characterizing a first phase offset between the fifth ligament tension curve and the first target tension curve;
characterizing a first amplitude difference between the fifth ligament tension curve and the first target tension curve;
characterizing a second phase offset between the sixth ligament tension curve and the second target tension curve;
characterizing a second amplitude difference between the sixth ligament tension curve and the second target tension curve;
in response to the second amplitude difference exceeding a threshold amplitude difference:
 accessing models of a kit of available spacer geometries;
 selecting a first spacer geometry defining a first spacer height from the kit of available spacer geometries based on the first amplitude difference, the second implant geometry, and the current set of bone resection parameters; and
 rendering a second prompt, on the display, to insert a spacer of the first spacer geometry between the first test implant and the second bone proximal the second ligament; and in response to the second phase offset exceeding the threshold negative phase offset:
rendering a third prompt, on the display, to further resect the first bone proximal the second ligament proportional to the second phase offset.

12. The method of claim 1, further comprising:
accessing models of a kit of available spacer geometries;
characterizing a first amplitude difference between the third ligament tension curve and the first target tension curve;
characterizing a second amplitude difference between the fourth ligament tension curve and the second target tension curve; and
in response to the first amplitude difference exceeding a threshold amplitude difference:
selecting a first spacer geometry defining a first spacer height, in the kit of available spacer geometries, based on the first amplitude difference and the first implant geometry; and
rendering a second prompt, on the display, to insert a spacer of the first spacer geometry between the first test implant and the second bone.

13. The method of claim 12, further comprising calculating the threshold amplitude difference based on the kit of available spacer geometries, a kit of available implant geometries, the first target tension curve, and the second target tension curve.

14. The method of claim 12, wherein selecting the first spacer geometry comprises, in response to the second amplitude difference falling below the threshold amplitude difference, selecting the first spacer geometry defining:
the first spacer height proximal a first side of the first bone adjacent the first ligament; and
a second spacer height less than the first spacer height proximal a second side of the first bone adjacent the second ligament.

15. The method of claim 12, further comprising:
at a third time succeeding the second time and succeeding insertion of the spacer into the knee:
generating a fifth ligament tension curve for the first ligament;
generating a sixth ligament tension curve for the second ligament;
characterizing a third amplitude difference between the fifth ligament tension curve and the first target tension curve; and
characterizing a fourth amplitude difference between the sixth ligament tension curve and the second target tension curve; and
in response to the fourth amplitude difference exceeding a threshold negative amplitude difference:
selecting a second spacer geometry from the kit of available spacer geometries based on the fourth amplitude difference, the second spacer geometry defining:
the first spacer height proximal a first side of the first bone adjacent the first ligament; and
a second spacer height greater than the first spacer height proximal a second side of the first bone adjacent the second ligament; and
rendering a third prompt, on the display, to exchange the first spacer with a second spacer of the second spacer geometry.

16. A method for generating intraoperative surgical guidance during a knee arthroplasty, comprising:
by a computer system at a first time preceding resection of a first bone in a knee of a patient:
accessing a first set of angular positions of the knee, output by an angular position sensor coupled to the knee, during articulation of the knee within a first test period;
transforming the first set of angular positions into a first set of lengths of a first ligament during articulation of the knee within the first test period;
accessing a first set of forces on the first ligament, output by a force sensor inserted into the knee proximal the first ligament, during articulation of the knee within the first test period; and
generating a first ligament tension curve for the first ligament in the knee based on the first set of forces on the first ligament and the first set of lengths of the first ligament;
storing a target tension curve, representing a target postoperative relationship between tensions on the first ligament and lengths of the first ligament over the first set of angular positions of the knee, based on the first ligament tension curve; and
by the computer system at a second time succeeding resection of the first bone and succeeding placement of a first test implant on the first bone:
accessing an interoperative set of angular positions of the knee, output by the angular position sensor coupled to the knee, during articulation of the knee within an interoperative test period;
transforming the interoperative set of angular positions into an interoperative set of lengths of the first ligament during articulation of the knee within the interoperative test period;
accessing an interoperative set of forces on the first ligament, output by the force sensor inserted into the knee proximal the first ligament, during articulation of the knee within the interoperative test period; and
generating a second ligament tension curve representing an interoperative relationship between tensions on the first ligament and lengths of the first ligament over the first set of angular positions of the knee resulting from placement of the first test implant on the first bone;
calculating a phase offset between the second ligament tension curve and the target tension curve; and
in response to the first phase offset exceeding a threshold negative phase offset:
transforming the first phase offset into a first resection difference; and
rendering a first prompt, on a display, to further resect the first bone, proximal the first ligament, by the first resection difference.

17. A method for generating intraoperative surgical guidance during a knee arthroplasty, comprising:
by a computer system at a first time preceding resection of a first bone in a knee of a patient:
accessing a first set of angular positions of the knee, output by an angular position sensor coupled to the knee, during articulation of the knee within a first test period;
transforming the first set of angular positions into a first set of lengths of a first ligament during articulation of the knee within the first test period;
accessing a first set of forces on the first ligament, output by a force sensor inserted into the knee proximal the first ligament, during articulation of the knee within the first test period; and generating a first ligament tension curve for the first ligament in the knee based on the first set of forces on the first ligament and the first set of lengths of the first ligament;

storing a target tension curve, representing a target postoperative relationship between tensions on the first ligament and lengths of the first ligament over the first set of angular positions of the knee, based on the first ligament tension curve; and by the computer system at a second time succeeding resection of the first bone and succeeding placement of a first test implant on the first bone:

accessing an interoperative set of angular positions of the knee, output by the angular position sensor coupled to the knee, during articulation of the knee within an interoperative test period;

transforming the interoperative set of angular positions into an interoperative set of lengths of the first ligament during articulation of the knee within the interoperative test period;

accessing an interoperative set of forces on the first ligament, output by the force sensor inserted into the knee proximal the first ligament, during articulation of the knee within the interoperative test period; and generating a second ligament tension curve representing an interoperative relationship between tensions on the first ligament and lengths of the first ligament over the first set of angular positions of the knee resulting from placement of the first test implant on the first bone;

calculating a first geometry difference between the second ligament tension curve and the target tension curve; and in response to the first geometry difference exceeding a threshold geometry difference:

based on the first geometry difference, identifying a target implant, from a kit of implants, predicted to the reduce the first geometry difference when located on the first bone in replacement of the first test implant, the target implant defining a geometry proximal the first ligament different from the first test implant; and rendering a first prompt, on a display, to replace the first test implant with the target implant.

18. The method of claim 17:
further comprising:
by the computer system at the first time preceding resection of the first bone and the second bone in the knee of the patient:

transforming the first set of angular positions into a second set of lengths of a second ligament during articulation of the knee within the first test period;

accessing a second set of forces on the second ligament, output by the force sensor inserted into the knee proximal the second ligament, during articulation of the knee within the first test period; and generating a second ligament tension curve for the second ligament in the knee based on the second set of forces on the second ligament and the second set of lengths of the second ligament;

storing a second target tension curve, representing a second target postoperative relationship between tensions on the second ligament and lengths of the second ligament over the second set of angular positions of the knee, based on the second ligament tension curve; and by the computer system at the second time succeeding resection of the second bone and succeeding placement of the first test implant on the second bone:

accessing a second interoperative set of angular positions of the knee, output by the angular position sensor coupled to the knee, during articulation of the knee within the interoperative test period;

transforming the second interoperative set of angular positions into a second interoperative set of lengths of the second ligament during articulation of the knee within the interoperative test period;

accessing a second interoperative set of forces on the second ligament, output by the force sensor inserted into the knee proximal the second ligament, during articulation of the knee within the interoperative test period; and generating a fourth ligament tension curve representing a second interoperative relationship between tensions on the second ligament and lengths of the second ligament over the second set of angular positions of the knee resulting from placement of the first test implant on the second bone; and calculating a second geometry difference between the second ligament tension curve and the target tension curve; and wherein identifying the target implant comprises, in response to the first geometry difference exceeding the threshold geometry difference and in response to the second geometry difference falling below the threshold geometry difference:

identifying the target implant, from the kit of implants, predicted to the reduce the first geometry difference and preserve the second geometry difference when located on the first bone in replacement of the first test implant, the target implant defining a geometry proximal the first ligament different from the first test implant and defining a second geometry proximal the second ligament analogous to the first test implant.

* * * * *